(12) United States Patent
Merchant (10) Patent No.: US 8,497,107 B2
(45) Date of Patent: Jul. 30, 2013

(54) COVALENTLY IMMOBILIZED ENZYME AND METHOD TO MAKE THE SAME

(75) Inventor: Stephen A. Merchant, Norman, OK (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 737 days.

(21) Appl. No.: 12/552,332

(22) Filed: Sep. 2, 2009

(65) Prior Publication Data
US 2010/0078381 A1 Apr. 1, 2010

Related U.S. Application Data

(60) Provisional application No. 61/101,302, filed on Sep. 30, 2008.

(51) Int. Cl.
*C12N 11/14* (2006.01)
*C02F 1/00* (2006.01)

(52) U.S. Cl.
USPC ........ 435/176; 210/198.1; 210/632; 435/177; 435/180

(58) Field of Classification Search
None
See application file for complete search history.

(56) References Cited

U.S. PATENT DOCUMENTS

| | | | |
|---|---|---|---|
| 3,669,878 A | 6/1972 | Marantz et al. |
| 3,989,622 A | 11/1976 | Marantz et al. |
| 4,138,292 A | 2/1979 | Chibata et al. |
| 4,141,857 A | 2/1979 | Levy et al. |
| 4,247,393 A | 1/1981 | Wallace |
| 4,266,029 A | 5/1981 | Branner-Jørgensen |
| 4,268,419 A | 5/1981 | Rohrbach |
| 4,268,423 A | 5/1981 | Rohrbach et al. |
| 4,342,834 A | 8/1982 | Wood et al. |
| 4,382,070 A | 5/1983 | Novak et al. |
| 4,434,228 A | 2/1984 | Swann |
| 4,438,196 A | 3/1984 | Lantero, Jr. |
| 4,478,938 A | 10/1984 | Freedman |
| 4,525,456 A | 6/1985 | Rohrbach |
| 4,581,141 A | 4/1986 | Ash |
| 4,978,619 A | 12/1990 | Kajiwara et al. |
| 5,618,710 A | 4/1997 | Navia et al. |
| 5,916,789 A | 6/1999 | Webbers et al. |
| 6,627,164 B1 | 9/2003 | Wong |
| 6,878,283 B2 | 4/2005 | Thompson |
| 7,033,498 B2 | 4/2006 | Wong |

(Continued)

FOREIGN PATENT DOCUMENTS

| | | |
|---|---|---|
| CN | 1660419 A | 8/2005 |
| EP | 0 132 998 | 2/1985 |

(Continued)

OTHER PUBLICATIONS

Partial International Search issued in corrresponding International Patent Application No. PCT/US2009/055647 dated Dec. 9, 2009 (2 pages).
Cobe Renal Care, Inc., "Guide to Custom Dialysis," Product No. 306100-005, Revision E, Sep. 1993, pp. 1-52 (54 pages).
Cobe Renal Care, Inc., "Sorbent Dialysis Primer," Product No. 306100-006, Edition 4, Sep. 1993, pp. 1-46 (56 pages).

(Continued)

*Primary Examiner* — Dirk Bass
(74) *Attorney, Agent, or Firm* — Kilyk & Bowersox, P.L.L.C.

(57) ABSTRACT

A composition of enzyme, polymer, and crosslinker forms a network of covalently bound macromolecules. The covalently immobilized enzyme preparation has enzymatic activity, and retains stable activity when dried and stored at ambient conditions. Methods for preparing an immobilized enzyme and methods for using the enzyme are disclosed.

42 Claims, 2 Drawing Sheets

U.S. PATENT DOCUMENTS

| | | | |
|---|---|---|---|
| 7,166,451 B1 | 1/2007 | Yang et al. | |
| 2002/0155425 A1* | 10/2002 | Han et al. | 435/4 |
| 2003/0098270 A1* | 5/2003 | Thompson | 210/283 |
| 2003/0105424 A1 | 6/2003 | Karoor et al. | |
| 2003/0232895 A1* | 12/2003 | Omidian et al. | 521/99 |
| 2004/0203149 A1* | 10/2004 | Childs et al. | 435/404 |
| 2005/0150832 A1 | 7/2005 | Tsukamoto | |
| 2005/0194304 A1 | 9/2005 | Paolis | |
| 2006/0140840 A1 | 6/2006 | Wong | |
| 2007/0111289 A1 | 5/2007 | Yang et al. | |
| 2007/0179431 A1 | 8/2007 | Roberts et al. | |

FOREIGN PATENT DOCUMENTS

| | | |
|---|---|---|
| GB | 1 517 813 | 7/1978 |
| JP | 51-128485 | 11/1976 |
| JP | 54-110385 | 8/1979 |
| JP | 58-086085 | 5/1983 |
| JP | 59-232092 | 12/1984 |
| JP | 60-137290 | 7/1985 |
| JP | 60-137433 | 7/1985 |
| JP | 60-221088 | 11/1985 |
| JP | 03-219873 | 9/1991 |
| WO | WO 92/08790 | 5/1992 |
| WO | WO 01/74928 A1 | 10/2001 |
| WO | WO 03/050234 A2 | 6/2003 |

OTHER PUBLICATIONS

Merchant, S.; "The Development of Redox Polymers Based on Linear Poly(ethylenimine) for Application in Amperometric Biosensors," A Dissertation submitted to the Graduate Faculty, University of Oklahoma Graduate College, 2007 (128 pages).

Merchant et al., "Effects of Electrolyte and pH on the Behavior of Cross-Linked Films of Ferrocene-Modified Poly(ethylenimine)," Langmuir, vol. 23, No. 22, 2007, pp. 11295-11302.

Merchant et al., "High-Sensitivity Amperometric Biosensors Based on Ferrocene-Modified Linear Poly(ethylenimine)," Langmuir, vol. 25, No. 13, 2009, pp. 7736-7742.

Erlenkötter et al., "Biosensors and flow-through system for the determination of creatinine in hemodialysate," Anal. Bioanal. Chem., vol. 372, 2002, pp. 284-292.

Joshi et al., "Amperometric Biosensors Based on Redox Polymer—Carbon Nanotube—Enzyme Composites," Analytical Chemistry, vol. 77, No. 10, May 15, 2005, pp. 3183-3188.

International Search Report and Written Opinion issued in corresponding International Patent Application No. PCT/US2009/055647 dated Apr. 26, 2010 (23 pages).

* cited by examiner

COVALENTLY IMMOBILIZED ENZYME AND METHOD TO MAKE THE SAME

This application claims the benefit under 35 U.S.C. §119(e) of prior U.S. Provisional Patent Application No. 61/101,302, filed Sep. 30, 2008, which is incorporated in its entirety by reference herein.

FIELD OF THE INVENTION

The present invention relates to the immobilization of an enzyme in a formation of covalently bound macromolecules (e.g., polymer, protein, starch). The enzyme can be covalently immobilized and retain stable enzyme activity when dried.

BACKGROUND OF THE INVENTION

Enzymes are proteinaceous in nature and act as biocatalysts to regulate many and varied chemical reactions. They are used in many analytical, medical and industrial applications. For example, enzymes find use in medical applications in dialysis systems to provide an artificial replacement for lost kidney function due to renal failure. The enzyme urease is used to convert urea to ammonia and carbon dioxide in hemodialysis and peritoneal dialysis systems. Many applications of enzyme functionality require the use of enzymes in aqueous systems at specific, fixed locations. A number of enzyme immobilization techniques have been employed to accomplish this including physical entrapment or adsorption, chemical adsorption, electrostatic adsorption, hydrogen bonding, covalent bonding, crosslinking, and encapsulation or microencapsulation. These techniques have not, however, made a dry, solid, enzyme crosslinked product that is stable as a dry, solid composition. Further complicating these efforts is the highly sensitive structure-function relationship which is generally unstable in many enzymes, and therefore subject to disruption through changes in temperature and pH, hydrolysis, and chemical or physical modification. These disruptions typically result in deactivation, or a diminished biocatalytic capacity of the enzyme.

Urease is an enzyme used in kidney dialysis treatment systems. Urease is used, for example, in sorbent dialysis to convert the urea in dialysate into ammonium and bicarbonate. These by-products, and others, can then be removed by sorbent materials, such as activated carbon and ion-exchange materials, so that fresh dialysate can be regenerated. Because this type of dialysis system involves flowing water through a layer of water-soluble enzyme, the immobilization of urease is important for at least the following reasons: (i) if not immobilized, the enzyme can dissolve into the flowing water and be transported throughout the system, effectively rinsing it away from its desired location and rendering the dialysate treatment system useless in a very short period of time; (ii) at the same time, the dissolved enzyme can be transported back to the patient by diffusion into the patient fluid, at which point, any urea in the patient would be converted into ammonium inside the patient.

The stability of urease with respect to its activity, or its capacity to catalyze the hydrolysis of urea, is often the source of failure for covalently immobilized, or crosslinked, urease materials. This instability translates to a short shelf-life making most crosslinked urease materials unfeasible for use in consumer products. Attempts aimed at improving the stability of the enzyme in the crosslinked state have included freeze drying, storage in liquid buffers, storage at low temperatures, or some combination of all of these methods. In addition to very limited success, the cost and logistical complications associated with each of these methods often reduces the employment of crosslinked urease to academic exercises.

There have been cost implications in the past with maintaining the stability of crosslinked urease materials. In addition to this, there can be a high cost prohibitive expense of using purified urease as the enzyme source. Almost all methods and materials involving crosslinked urease employ a purified form of the enzyme. Aside from the limited amount of success achieved with these materials, the expense associated with purifying urease poses a major obstacle in the development of consumer products on a wide scale.

A need exists for immobilized enzymes that are stably bound and not capable of dissolution or displacement into a liquid phase. A further need exists for immobilized enzymes that possess a high level of enzymatic activity and maintain steady activity when stored for long periods under ambient conditions. Another need exists for immobilized enzymes that can be produced from economically feasible sources.

SUMMARY OF THE INVENTION

A feature of the present invention is to provide an immobilized enzyme that avoids one or more of the above-mentioned disadvantages.

A further feature of the present invention is to provide a composition comprising a covalently immobilized enzyme in a formation of covalently bound macromolecules.

Another feature of the present invention is to provide a composition comprising a covalently immobilized enzyme that can be dried and stored and retain enzymatic activity.

A further feature of the present invention is to provide an immobilized enzyme that can be utilized in a system for removing a compound (or substance) from the system.

Another feature of the present invention is to provide a sorbent cartridge for dialysis comprising immobilized enzyme in a formation of covalently bound macromolecules.

Another feature of the present invention is to provide a method for preparing an immobilized enzyme that retains enzymatic activity.

A further feature of the present invention is to provide a method for preparing an immobilized enzyme that is covalently bound.

Another feature of the present invention is to provide a method for preparing an immobilized enzyme that can utilize crude (or raw) unpurified forms of the enzyme.

Additional features of the present invention will be set forth in part in the description that follows, and in part will be apparent from the description, or may be learned by practice of the present invention. The features of the present invention can be realized and attained by means of the elements particularly pointed out in the appended claims.

To achieve the above noted features and in accordance with the purposes of the present invention, as embodied and broadly described herein, the present invention provides a composition comprising a covalently immobilized enzyme and having enzymatic activity. The composition can comprise a reaction product of the enzyme, a polymer, and a crosslinker. The composition can comprise a formation of covalently bound macromolecules, and the enzyme can be covalently bound to the crosslinker and to the polymer. The composition can be dried and then stored under ambient temperature and pressure and yet maintain enzymatic activity. This type of immobilization can prevent the dissolution of the enzyme into a liquid phase. This type of immobilization can also prevent the displacement of enzyme from its immobilized state by other chemicals or biochemicals and/or prevent the migration of enzyme as a consequence of support failure.

The present invention also provides a method for preparing an immobilized enzyme. The method can comprise forming an aqueous mixture of a polymer and the enzyme, adding a crosslinker to the aqueous mixture to form a reaction mixture, and maintaining the reaction mixture for a time sufficient to crosslink the reaction mixture in a formation of covalently bound macromolecules.

The present invention also provides a method for removing a compound (or substance) from a system containing the compound (or substance). The method can comprise treating the system with a composition comprising a covalently immobilized enzyme having enzymatic activity and recovering a system substantially free of the compound (or substance). The enzyme can be immobilized such that it does not dissolve and does not leak or migrate into the system.

The present invention thus provides a sorbent cartridge comprising a covalently immobilized enzyme having enzymatic activity in the sorbent cartridge.

It is to be understood that both the foregoing general description and the following detailed description are exemplary only and are not restrictive of the present invention, as claimed.

DETAILED DESCRIPTION OF THE INVENTION

Figure 1:
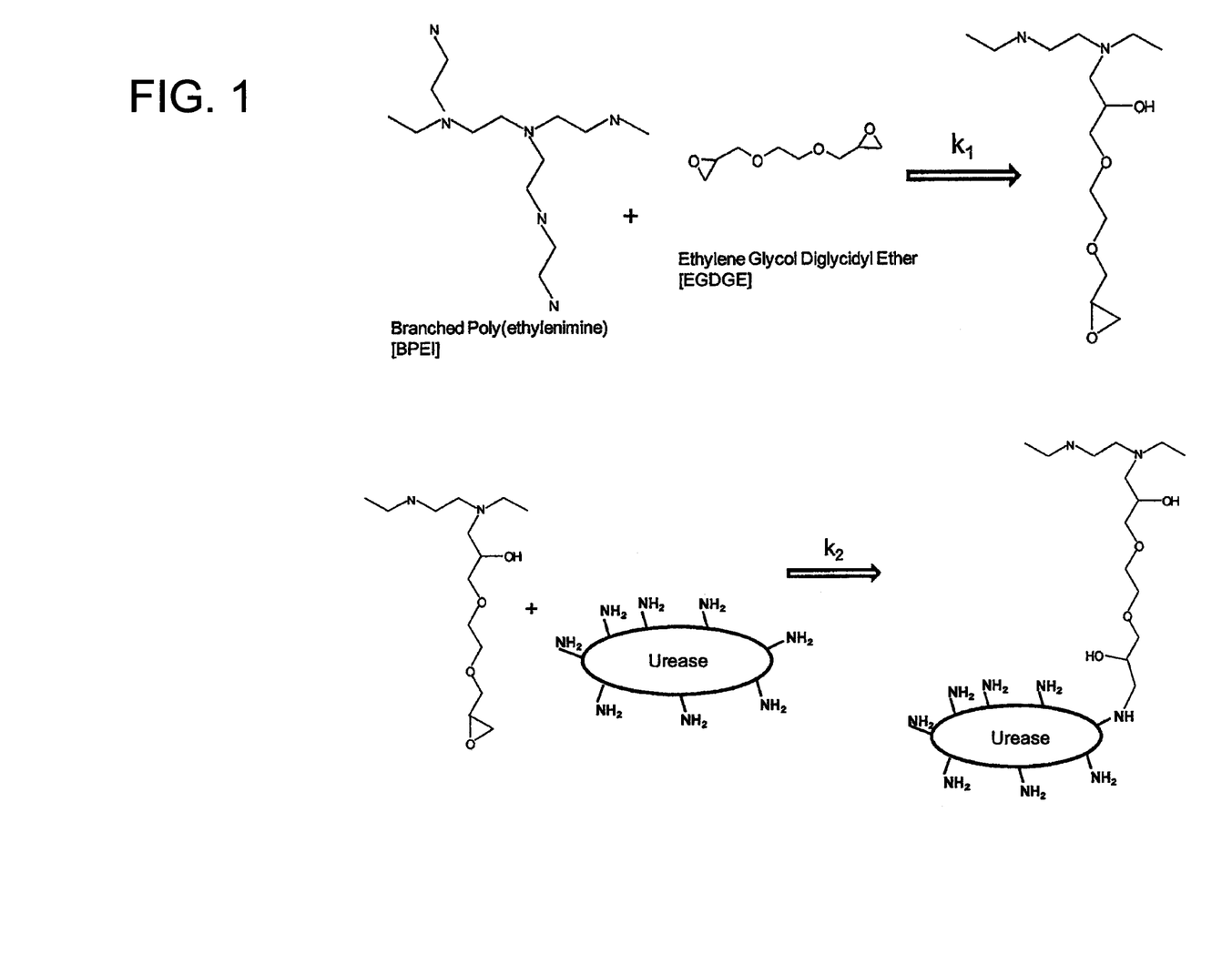
FIG. 1 is a schematic illustration of the chemistry involved in a method of enzyme immobilization according to the present invention.

The present invention relates to a composition comprising a covalently immobilized enzyme having enzymatic activity. The composition can comprise the enzyme, polymer, and crosslinker, in a formation of covalently bound macromolecules. The composition can comprise a reaction product of enzyme, polymer, and crosslinker, such as that shown, for example, in FIG. 1. As shown in FIG. 1, an enzyme (e.g., urease) can be covalently immobilized in a formation of macromolecules with a polymer (e.g., branched poly(ethylenimine) and a crosslinker (e.g., ethylene glycol diglycidyl ether). The immobilized enzyme can be covalently bound to the polymer and/or crosslinker, and can retain enzyme activity. In the present invention, more than one enzyme, and/or more than one polymer, and/or more than one crosslinker can be used or present. The crosslink density of the composition can be from 1% to 50% or more, such as from 9% to 50%, with respect to the % of the available functional groups on the polymer (e.g., nitrogen atoms on the polymer). The composition, which is preferably a hydrogel, can have a water swelling rate of 50% to 250% compared to its dry state.

In the present invention, the composition can be a solid, wherein the enzyme can be uniformly present throughout the composition. Thus, and as an option, the composition can be formed into particles or powder, such as by milling or grinding, and each particle has the enzyme present due the enzyme being part of the reaction and being crosslinked to the polymer by way of the crosslinker(s). Since the composition can be a solid and in particle form, the particles can have any size and shape, such as, but not limited to, an average particle size of from about 10 microns to about 10 millimeters, such as from about 20 microns to 1 millimeter, or from 25 microns to 75 microns. The particles are preferable rigid and/or flowable. The particle shape can be uniform, irregular, spherical, platelet, or the particles can have other shapes.

The composition, when a solid, can have a low water content or moisture content, such on the order of 25 wt % or less, 15 wt % or less, 10 wt % or less, 5 wt % or less, such as from 0.1 wt % to 15 wt %, 1 wt % to 10 wt %, 5 wt % to 10 wt %, based on the weight of the solid composition.

The polymer can be a homopolymer, copolymer, or terpolymer, or the like. The polymer can comprise, for example, a polyamine. The polymer can have one or more of the following characteristics: (i) polymer flexibility or high segmental mobility, (ii) a high degree of functional density on the polymer to facilitate modification and cross-linking, and/or (iii) a polymer that hydrates. The polymer can comprise, for example, linear poly(ethylenimine), branched poly(ethylenimine), linear or branched poly(propylenimine), poly(allylamine), poly(vinylpyridine), poly(vinylimidazole), poly(l-lysine), or any combination thereof.

Poly(ethylenimine) (PEI), for example, has all of the above characteristics. PEI can be obtained in a branched (BPEI) or a linear (LPEI) form. Both the linear and branched forms have glass transition temperatures (LPEI $T_g$=$-35°$ C., BPEI $T_g$=$-50°$ C.) that indicates that, at room temperature or higher, they should exhibit a high degree of segmental mobility.

PEI polymers have a high degree of amines in their structure that allows one to easily modify the polymer. BPEI contains approximately equal numbers of primary and tertiary amines, and these account for about half of the amino groups in the polymer, with the other half of the total number of amino groups being secondary amines. On the other hand, the amino groups in LPEI are almost exclusively secondary amines, with the exception of the primary amines at each end of the polymer chains. Various moieties, for example, enzymes, can be easily attached to the polymer through the primary (BPEI) and secondary (LPEI) amine groups. This can also allow one to vary the degree of enzyme binding and control cross-link density.

An additional attractive feature of PEI is that it can enhance several enzyme properties. PEI by itself can enhance the long-term storage stability of enzymes in solution and during freeze drying, as well as increasing the sensitivity and stability of enzymes. Furthermore, protonated forms of PEI at low pH can exist in an extended state as a result of the electrostatically repulsive positive charges on the polymer backbone, and have been shown to be quite soluble in water. The other polymers that can be used herein can have one or more of these characteristics as well.

The polymer in general is not limited to any molecular weight ($M_w$) or number average molecular weight ($M_n$). The polymer can have, for example, an average $M_w$ in a range of from about 1 kilodalton (kDa) to about 1000 kDa, and a $M_n$ in a range of from about 1 kDa to about 100 kDa. BPEI (available from Sigma-Aldrich), for example, can have an average $M_w$ (by LS) of about 1.3 kDa, about 2.0 kDa, about 25 kDa, or about 750 kDa, and an $M_n$ (by GPC) of about 1.2 kDa, about 1.8 kDa, about 10 kDa, or about 60 kDa. Other molecular weights and number average molecular weights are possible.

The polymer can be present in the composition in an amount without limitation, for example, from about 1 weight percent to about 90 weight percent, from about 5 weight percent to about 75 weight percent, from about 10 weight percent to about 50 weight percent, or from about 25 weight percent to about 35 weight percent by weight of the composition.

The crosslinker can comprise a bi- or poly-functional reagent which can form covalent bonds with the enzyme and/or the polymer. The crosslinker can comprise, for example, one or more epoxy groups, one or more acrylate groups, one or more halide groups, one or more carboxyl groups, one or more aldehyde groups, or any combinations thereof. Examples of suitable crosslinkers are heterobifunctional polyethylene glycol, homobifunctional polyethylene glycol, or combinations thereof.

The crosslinker can have flexibility or segmental mobility. A crosslinker having flexibility can have a better opportunity to covalently bind to an enzyme and at the same time allows the enzyme to maintain and present an enzyme active site for the substrate. The crosslinker can comprise, for example, poly(ethylene glycol)diacrylate, tetra(ethylene glycol)diacrylate, poly(ethylene glycol)diglycidyl ether, ethylene glycol diglycidyl ether, dibromohexane, gluteraldehyde, epichlorohydrin, or any combination thereof.

The crosslinker can be present in an amount to crosslink at least a portion of the polymer and/or enzyme, such as from about 1 wt % to 20 wt %, based on the weight of the composition.

The enzyme can be covalently bound to the crosslinker and/or to the polymer. Any enzyme can be used in the present invention. Examples of suitable enzymes include invertases, glucosidases, lactases, maltases, amylases, hydrolases, ureases, lipases, esterases, isomerases, oxidases, and dehydrogenases. More specific examples include glucose oxidase, lactate oxidase, sarcosine oxidase, peroxidase, creatinase, creatininase, glucose dehydrogenase, urease, or any combination thereof. Mixtures of one or more enzyme can also be employed in the method so that the resulting formation of covalently bound macromolecules can have more than one enzymatic activity.

With the present invention, a crude or raw enzyme material can be immobilized without the need to purify the enzyme, and this crude or raw enzyme material can be immobilized by the methods of the present invention to form the immobilized enzyme of the present invention, wherein the enzyme is crosslinked to the polymer by a crosslinker as described herein. The enzyme can comprise a purified or fractionated form of the enzyme, or it can comprise a crude form of the enzyme. Crude forms of the enzyme can provide a more economical method and composition. For example, the enzyme can comprise urease derived from natural sources, such as, but not limited to, jack beans (*Canavalia ensiformis*). Urease can also be derived from other natural sources, for example, soybeans (*Glycine max*), other legumes and plants, bacteria (e.g. *Bacillus pasteurii*), or yeast. Purified forms of urease can comprise, for example, fractionated or crystallized forms (Sigma-Aldrich, St. Louis, Mo.). When the crude or raw enzyme material is used, this crude or raw enzyme material can be characterized by its enzymatic activity as measured in SU/g. For instance, a crude or raw enzyme material can have or be characterized by its enzymatic activity so as to have an enzymatic activity ranging from about 100 SU/g to 1,000 SU/g (e.g., 100 to 500 SU/g, 150 to 300 SU/g). When the enzymatic material is a purified form or crystallized form or a fractionated form, the purity can be characterized by its enzymatic activity and be, for instance, in the range of from 2,000 SU/g to 6,000 SU/g or higher, for instance, from 2,500 SU/g to 5,500 SU/g. With the present invention, it was surprising to achieve enzyme stability as described herein for crude/raw enzyme material, as well as purified forms.

The composition can comprise an immobilized enzyme, wherein the enzyme retains enzymatic activity. The immobilized enzyme can retain, for example, from about 90 percent to about 100 percent activity, or at least 50 percent, at least 40 percent, at least 25 percent, or at least 10 percent (e.g., 10% to 95%, 15% to 90%, 20% to 85%, 25% to 80%, 30% to 75%, 35% to 70%, 40% to 65%, 45% to 60%) of the enzymatic activity compared to non-immobilized enzyme. The enzyme can be present in an amount, for example, of from about 0.5 weight percent to about 80 weight percent, from about 10 weight percent to about 75 weight percent, from about 20 weight percent to about 60 weight percent, or from about 30 weight percent to about 55 weight percent by weight of the composition. An example of the enzymatic activity of a composition comprising immobilized urease is illustrated in FIG. 2.

Figure 2:
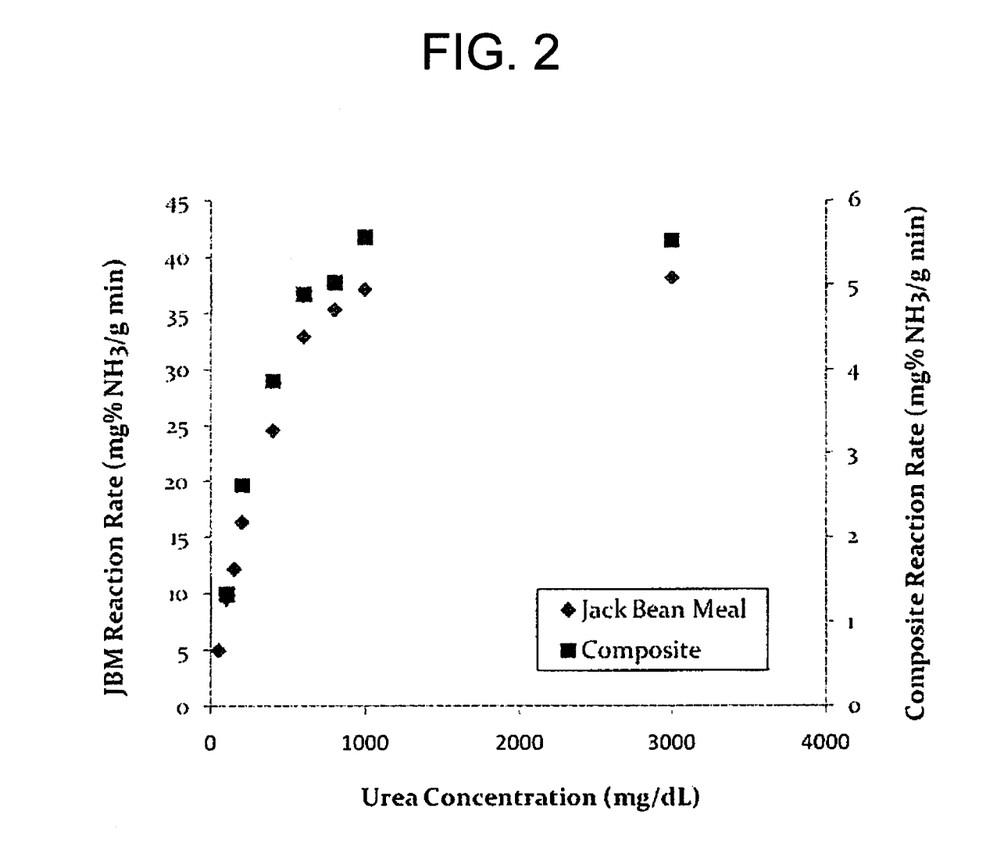
FIG. 2 is a graph representing the kinetics of urease activity in crude non-immobilized enzyme compared to immobilized enzyme according to the present invention.

In FIG. 2 the enzymatic activity of immobilized urease (Composite) and the enzymatic activity of crude urease utilized to make the composition (i.e., non-immobilized) (Jack Bean Meal) are shown. The immobilized enzyme composition demonstrates identical enzyme kinetics (i.e., $K_m$ JBM=Composite), and does not saturate any quicker than the crude urease. FIG. 2 also shows that the immobilized urease retains at least about 30-40% of its enzyme activity.

The composition can comprise a reaction product of at least one enzyme, at least one polymer, and at least one crosslinker in a formation of covalently bound macromolecules, wherein the reaction product results from a reaction between one or more functional groups in the crosslinker and the polymer, and a reaction between one or more functional groups in the crosslinker and the enzyme. Referring again to FIG. 1, the reaction product can result from a reaction between, for example, a first epoxy group of the crosslinker (EGDGE) and an amine group of the polymer (BPEI), and between a second epoxy group of the crosslinker and amine group of the enzyme (urease).

The composition can be a hydrogel. For purposes of this invention, a hydrogel can be defined as a network of polymer chains that are water-insoluble and swellable in water. The hydrogel can contain a significant amount of water, for example, it can contain over 99 wt % water, based on the weight of the hydrogel.

The composition can be dry. The composition can be dried, for example, to a water content (or moisture content) of from about 0 wt % to about 25 wt %, less than 15 wt %, less than 10 wt %, or from about 0 wt % to 15 wt %, 0.01 wt % to 5 wt %, 0.1 wt % to 1 wt %, 0.5 wt % to 10 wt %, 2 wt % to 8 wt %, or 5 wt % to 10 wt %, based on the weight of the composition. The immobilized enzyme can retain enzymatic activity when dried, and maintain that activity when stored in a dry state. The composition can retain, for example, greater than 10 percent, greater than 25 percent, greater than 50 percent, greater than 80 percent, greater than 90 percent, or about 100 percent enzymatic activity when stored at ambient temperature and pressure (e.g., 25° C. at 1 atm) for at least 1 week, at least 30 days, at least 60 days, at least 90 days, or for at least 6 months or more, compared to the initial enzymatic activity at 0 day (when formed).

The composition can further comprise additives, such as in the form of particles. The additives can comprise, for example, materials onto which the polymer/enzyme/crosslinker composition can adsorb. For example, the composition can optionally comprise activated carbon particles. The addition of activated carbon particles can alter, for example, the denseness and/or rigidity of the macromolecule composition. The more carbon particles present the more dense and rigid the composition. The activated carbon can adsorb the formation of covalently bound macromolecules, for example, by adsorbing the polymer. The activated carbon can have an average particle size of, for example, from about 1 micron to about 100 microns, from about 5 microns to about 80 microns, or from about 10 microns to about 50 microns. The activated carbon or other filler material or adsorbable material can be present in the composition in an amount of, for example, from about 0 weight percent to about 50 weight percent, from about 1 weight percent to about 30 weight percent, from about 5 weight percent to about 40 weight percent, or from about 10 weight percent to about 30 weight percent, based on the weight of the composition.

The composition can further comprise ion-exchange additives, such as in the form of particles, for example, anion exchange and/or cation exchange particles. The composition can comprise, for example, zirconium phosphate and/or zirconium oxide particles. The ion-exchange particles can be present in the composition in an amount of, for example, from about 0 weight percent to about 50 weight percent, from about 1 weight percent to about 30 weight percent, from about 5 weight percent to about 40 weight percent, or from about 10 weight percent to about 30 weight percent, based on the weight of the composition. Ion-exchange materials, in combination with, for example, immobilized urease, can provide a composition for use in kidney dialysis systems. The anions and/or cations present in dialysate, for example, $NH_4^+$, $Ca^+$, and/or $P^-$, can be adsorbed by the ion-exchange particles and removed from the dialysate.

The present invention further relates to methods for preparing an immobilized enzyme in a formation of covalently bound macromolecules wherein the enzyme has enzymatic activity and can retain the activity for a long period of time (e.g., at least 30 days) as disclosed earlier. The method can covalently attach the enzyme to a polymer and/or to a crosslinker, optionally with a controlled amount of crosslink density.

The method for preparing an immobilized enzyme can comprise forming an aqueous mixture of at least one polymer and at least one enzyme, and adding at least one crosslinker(s) to the aqueous mixture to form a reaction mixture, and maintaining the reaction mixture to immobilize the enzyme in a formation of covalently bound macromolecules. The method can comprise first dissolving the polymer in an aqueous solution, then adding the enzyme to the aqueous solution, and then adding the crosslinker to form the reaction mixture. Any other order of addition can be used.

In the reaction mixture, the crosslinker can comprise one or more functional groups that react with the polymer and/or the enzyme. For purposes of the present invention, the term "functional group," includes all chemical structures by which covalent and/or non-covalent interactions can take place. The one or more functional groups can comprise, for example, an epoxide, an acrylate, a halide, a carboxyl, an aldehyde, or any combination thereof. As shown by the example in FIG. 1, a first epoxy group of the crosslinker (EGDGE) can react with an amine group of the polymer (BPEI), and a second epoxy group of the crosslinker can react with an amine group of the enzyme (urease). The epoxy group can react with a primary amine present in, for example, lysine, and/or secondary or tertiary amines present in, for example, glutamine, arginine, asparagines, and/or histidine. Epoxides, for example, can be susceptible to nucleophiles, and other candidates that the epoxy groups can react with include, for example, thiol groups and carboxyl groups.

Referring again to FIG. 1, a method for preparing an immobilized enzyme, for example, immobilized urease is shown. As shown by the schematic in FIG. 1, a mixture comprising branched poly(ethylenimine) polymer (BPEI), ethylene glycol diglycidyl ether (EGDGE), and urease react to produce a formation of covalently bound macromolecules. In Reaction 1, two chemically active groups can be the amino groups of BPEI (the lone pair of electrons make them nucleophiles), and the epoxy groups of EGDGE. The nucleophilic amine attacks the least hindered carbon atom of the first epoxy group. In Reaction 2, the second epoxy group reacts with other available amine groups in the system. A portion of these can be the amine groups of the lysine residues from the urease, in addition to other functional groups supplied by the enzyme.

The sequence of these two reactions can be transposed. In other words, the epoxy groups can react with amines from the enzyme first, then with the polymer. In addition, crosslinking can occur from enzyme molecule to enzyme molecule, or BPEI chain to BPEI chain. Accordingly, a well-mixed, homogenous solution can optionally be achieved, before adding the crosslinker.

Depending on the choice of polymer, in some instances the polymer may not be readily soluble in water. The polymer can be made more soluble in water by adding an acid, for example, hydrochloric acid (HCl), to the aqueous solution, and/or by applying heat. Once the polymer is dissolved, the enzyme can be added. An electrostatic complex can be formed between the polymer and the enzyme that can stabilize the enzyme. The aqueous solution can be cooled, if necessary, to about room temperature, before adding the enzyme. The enzyme can be added at a higher temperature or a lower temperature, or at any temperature range over which the enzyme remains active, for example, a temperature range of about 20° C. to about 50° C. The enzyme can be added to the polymer solution and blended using, for example, a magnetic stirrer. As the polymer and enzyme solution mixes, the solution may become viscous and require stronger mixing techniques and/or manual mixing.

As one option, once a homogenous blend of polymer and enzyme is obtained, the crosslinker can then be added. The crosslinker can be added before, during, and/or after the blending of polymer and enzyme. This mixture can be blended together, for example, with vigorous mixing, to form a reaction mixture. The reaction mixture can then be poured onto a surface, for example, a non-stick surface, and allowed to cure. The reaction mixture can cure at any temperature range over which the enzyme remains active, for example, a temperature range of about 20° C. to about 50° C., or at ambient temperature (e.g., 25° C.). The curing time can range, for example, from less than an hour to about 24 hours, or about 2-4 hours. Once the mixture has cured, the material can be ground into smaller particles, for example, using a blender.

The ground particles, comprising the immobilized enzyme in a formation of covalently bound macromolecules, can be dried. The ground particles can be dried, for example, under ambient pressure (e.g., 1 atm), or under vacuum. The ground particles can be dried in a vacuum oven, for example, at a vacuum pressure of from about −5 inches Hg to about −27 inches Hg, or about −25 inches Hg. The particles can also be dried, for example, in a desiccator having a relative humidity of from about 1% to about 25%, for example about 10%. As a further example, the immobilized enzyme in the composition of the present invention, when, as a solid, can be dried by putting the solid immobilized enzyme composition of the present invention, for instance, in the form of ground particles, in a column and pumping argon or other inert gases through the column in order to dry the material. This can occur for 1 hour to 12 hours or more. This particular procedure or similar procedures can be done until a moisture content or water content of the ground particles is 15 wt % or less based on the weight of the composition. This initial drying is preferably occurring immediately after the solid is formed or within 1 hour or within 5 hours of the material being formed so as to reduce the moisture content or water content to 15 wt % or lower. After using the column with inert gas, other drying techniques, such as a vacuum oven, desiccator, or the like, can be used to reduce the moisture content or water content even further. As stated, the drying of the solid composition of the present invention preferably occurs within hours of its preparation to achieve a moisture content of 15 wt % or less. By doing so, a higher enzymatic starting activity can be achieved. The crosslinker can be added to the aqueous mixture in any amount to obtain a desired degree of crosslinking in the formation of covalently bound macromolecules. In some formulations, too much cross-linking can affect the enzyme activity and/or stability. A high degree of crosslinking can produce, for example, an immobilized enzyme having reduced enzyme activity, and/or lower stability. The crosslinker can be added in an amount to obtain, for example, a crosslink density of from about 0.5 percent to about 50 percent, from about 5 percent to about 30 percent, from about 10 percent to about 20 percent, about 40 percent, less than about 40 percent, about 20 percent, or about 10 percent.

As stated earlier, the method can further comprise blending additional additives, such as particles, into the mixture. The additional additives can comprise, for example, materials onto which the polymer/enzyme/crosslinker composition can adsorb. For example, activated carbon can be added to the mixture and blended to provide a homogenous mixture. The addition of activated carbon particle can alter, for example, the denseness and rigidity of the macromolecule composition. Ion-exchange materials, for example zirconium phosphate and/or zirconium oxide, can be added to the mixture.

The method can comprise preparing an immobilized enzyme in a formation of covalently bound macromolecules, drying the macromolecules, and storing the immobilized enzyme. The immobilized enzyme can be stored in a dry state at ambient temperature and pressure (e.g., 25° C. at 1 atm), and yet retain enzymatic activity. The immobilized enzyme can retain enzymatic activity for at least 30 days, such as 2-6 months, such that at least 10%, at least 20%, at least 30%, at least 40%, at least 50%, at least 60%, at least 70%, at least 80%, at least 90%, or at least 95% of the enzymatic activity remains compared to the activity on the day of preparation. Table 1 show the results of urease activity measured from an immobilized urease composition prepared by a method of the present invention, and detailed in Example 1, and stored at ambient temperature and pressure.

As shown in Table 1, urease activity was measured on the initial day of preparation (Day 0), and at daily intervals on several days thereafter. As shown by the data, the activity remained stable throughout, and on Day 82 retained at least as much enzymatic activity as that measured on Day 0.

TABLE 1

| Urease activity | |
|---|---|
| Days After Prep. | Activity of Material (SU/g) |
| 0 | 30.39 |
| 1 | 27.28 |
| 2 | 32.17 |
| 5 | 32.71 |
| 6 | 32.19 |
| 8 | 33.37 |
| 12 | 32.88 |
| 15 | 29.1 |
| 20 | 31.38 |
| 29 | 41.33 |
| 36 | 29.05 |
| 51 | 39.07 |
| 68 | 30.06 |
| 82 | 34.81 |
| 103 | 36.08 |
| 126 | 39.27 |
| 159 | 32.7 |
| 294 | 48.1 |
| 394 | 37 |
| 460 | 40 |

In the methods of the present invention, preferably, the polymer and enzyme are crosslinked in a single phase, e.g, an aqueous phase, wherein the enzyme (e.g., urease) can be dissolved in the aqueous phase and the polymer is reacted in the same aqueous phase. The polymer can be water-soluble.

The present invention further relates to a method for removing a compound (or substance) from a system containing the compound (or substance), utilizing an immobilized enzyme of the present invention as described herein. The method can comprise treating the system with a composition comprising a covalently immobilized enzyme and having enzymatic activity. The composition can be a reaction product of the enzyme, polymer, and crosslinker, in a formation of covalently bound macromolecules. The system can comprise, for example, a dialysis system, the compound (or substance) can comprise, for example, urea, and the enzyme can comprise, for example, urease. The method can further comprise treating the system with, for example, one or more ion-exchange materials.

A sorbent cartridge can comprise the composition described herein in the sorbent cartridge. The composition can comprise, for example, a covalently immobilized enzyme and having enzymatic activity. The composition can comprise a reaction product of the enzyme, polymer, and crosslinker, in a formation of covalently bound macromolecules. The sorbent cartridge can comprise one or more layers, for example, two layers, and at least one of the layers can comprise the composition of the present invention. The composition can comprise, for example, immobilized urease. The composition can further comprise activated carbon in the formation and/or other additives.

The present invention by way of using the composition of the present invention can avoid the need to have an alumina or similar layer above the enzyme layer in a dialysis (e.g., sorbent) cartridge, since the immobilization of the enzyme by the present invention is effective and accomplished by the crosslinking as discussed herein. Thus, one aspect of the present invention includes a dialysis cartridge or sorbent cartridge that include the composition of the present invention (e.g., as a layer) and does not include (or does not necessitate) an alumina layer or similar layer adjacent to the enzyme containing section or layer.

The composition of the present invention can be used in place of any enzyme or immobilized enzyme. The composition of the present invention can be used as the enzyme layer (e.g., urease) in the sorbent cartridge described in U.S. Pat. Nos. 6,627,164; 6,878,283; 7,033,498; or published Application No. 2006/0140840, incorporated by reference herein.

The composition can be used as a component in a dialysis cartridge or device. The dialysis cartridge can be a cartridge that contains the composition of the present invention, wherein the composition is present as at least one layer and the dialysis cartridge further can comprise at least one other layer(s) of sorbent material.

The composition of the present invention can be used in any application where an enzyme (such as urease) is used and can be used as the urease or enzyme layer or as an additional urease or enzyme layer in sorbent cartridges, such as one described in U.S. Published Patent Application No. 2002-0112609 and U.S. Pat. No. 6,878,283 B2, and in Sorb's REDY cartridge (e.g., see "Sorbent Dialysis Primer," COBE Renal Care, Inc. Sep. 4, 1993 edition, and "Rx Guide to Custom Dialysis," COBE Renal Care, Inc. Revision E, September 1993), all incorporated in their entirety by reference herein. All embodiments using an enzyme such as urease in these published documents/applications are embodiments of the present application wherein the composition of the present invention is used. For example purposes only, various filter media sections within a tubular housing or cartridge can be used with the composition of the present invention. The housing or cartridge can include a sorbent material like a granular activated carbon section, an immobilized enzyme section, an optional powdered alumina ($Al_2O_3$) section, a zirconium phosphate, and/or a section that includes a mixture of hydrous zirconium oxide of the acetate form and sodium zirconium carbonate, or sodium zirconium carbonate alone. The dialysis cartridge can be a cartridge that contains as one or more layers or zones the composition of the present invention, wherein the dialysis cartridge has a plurality of filter media sections (or layers) including an arrangement, starting from a first end and ending at a second end, an activated carbon section, an immobilized enzyme section, an optional powdered alumina section, a zirconium phosphate section, and a sodium zirconium carbonate or a mixture of hydrous zirconium oxide of the acetate form and sodium zirconium carbonate section. For hemodialysis, a filter medium adapted to remove chlorine from tap water is preferred unless highly purified water is used as a base for the dialysate. The medium can be activated carbon. Activated carbon can be used as a filter medium to bind heavy metals, oxidants, and chloramines. An immobilized enzyme such as urease can be used in a filter medium to convert urea to ammonium carbonate by enzymatic conversion. Alumina ($Al_2O_3$), activated carbon, anion exchange resins, and/or diatomaceous earth can be used as adsorbents. The use of activated carbon to remove chlorine, if used, can precede the immobilized enzyme medium because chlorine can deactivate the enzyme. Cation exchange materials can be used to bind ammonium, calcium, magnesium, potassium, and other cations as well as toxic trace metals in tap water. Another function of these filter media can be to convert carbonate from urea hydrolysis to bicarbonate. Such cation exchange materials can include zirconium phosphate, titanium phosphate, or zeolite. Anion exchange filter media bind phosphate, fluoride, and other heavy metals. By-products of the anion exchange filter media can include acetate and bicarbonate, which also corrects for metabolic acidosis of a patient's blood. Such filter media can include hydrous zirconium oxide of the acetate form, hydrous silica, stannic oxide, titanium oxide, antimonic acid, hydrous tungsten oxide, or sodium zirconium carbonate.

The following examples are given to illustrate the nature of the invention. It should be understood, however, that the present invention is not limited to the specific conditions or details set forth in these examples.

EXAMPLES

In the examples, the urease activity was determined according to the following reagents/procedure:

Reagents

Ammonia Sulfate Stock Solution (2000 mg % $NH_3$—N): Dissolve 94.34 grams of $(NH_4)_2SO_4$ in $H_2O$. Add 1 drop concentrated $H_2SO_4$. Make to one (1) liter.

Phenol Reagent: Dissolve 50 grams phenol and 0.25 grams sodium nitroprusside (sodium nitroferricyanide) in $H_2O$ and make to one (1) liter with $H_2O$.

Hypochlorite Reagent: Dissolve 25 grams NaOH in about 500 ml $H_2O$. Add 20 ml of 10% sodium hypochlorite bleach and make to one (1) liter with $H_2O$.

$NH_3$—N Standards (10 mg %, 15 mg %, and 20 mg %): Pipette 0.5 ml, 0.75 ml and 1 ml of Ammonia Sulfate Stock Solution (2000 mg %) into respective 100 ml Volumetric flasks and make to volume with $H_2O$.

Procedure

Run all standards, samples, and blanks in triplicate.
Add 1 ml of Phenol Reagent to all test tubes.
Add 20 ul of $H_2O$ to respective test tube as blank.
Add 20 ul of Standards to respective test tubes.
Mix.
Add 1 ml of Hypochlorite Reagent and vortex.
Allow to stand at room temperature for 20 minutes.
Add 8 ml of $H_2O$ and vortex three (3) times.
Read absorbance at 635 nm using blank in the reference cuvette (as applicable).
Calculate mg % $NH_3$—N in sample by comparing absorbance of sample to absorbance of Standards.

Example 1

Preparation of BPEI/EGDGE/Urease/Carbon Composition with 10% Crosslink Density (Batch 15)

Ten (10) g BPEI were dissolved in 25 mL of 5 M HCl by adding the acid very slowly (dropwise) onto the stirring polymer. This took about 30-45 min. Once all acid was added, the polymer solution was allowed to stir until cooled to room temperature. This took about 10 min.

Fifteen (15) g of Jack Bean Meal (JBM) were blended with 5 g of activated carbon powder. This blend was then added to the cooled polymer solution and stirred. At a certain point, the magnetic stirrer was not strong enough to stir. The mixture was then stirred vigorously with a spatula as a whisk.

Once homogenous, 1.75 mL of EGDGE (TCI America, Polysciences, SPI Supplies) was added. A common name for this crosslinker is Quetol 651. Using the spatula, the mixture was again mixed vigorously.

The mixture was then poured onto a non-stick surface (i.e., a plastic bucket lid) and allowed to cure for approximately 3 hours in ambient conditions. The composition was then placed in a blender and ground into small particles.

The particles were then placed in a vacuum oven held at 25° C. and dried for 24 hours at −25 inches Hg (vacuum). The particles were then removed from the vacuum oven and placed in a desiccator with a relative humidity of about 10% for another 24 hours to completely dry.

The dried weight was 32-34 g. If the weight was higher, then the material was returned to the desiccator for further drying.

The crosslink density was calculated to be approximately 10%. Urease activity of Batch 15 was measured by the procedure detailed above and in Example 4.
Results:

| Standards | 1 | 2 | 3 | avg | stdev |
|---|---|---|---|---|---|
| 10 | 0.317 | 0.312 | 0.318 | 0.316 | 0.0035 |
| 15 | 0.479 | 0.489 | 0.485 | 0.484 | 0.0070 |
| 20 | 0.661 | 0.633 | 0.658 | 0.651 | 0.0198 |

| | 1 | 2 | 3 | avg | stdev |
|---|---|---|---|---|---|
| Batch 15 | 1.052 | 1.043 | 1.036 | 1.044 | 0.0080 | mg % $NH_3$ in Batch 15 samples: 30.39
Activity of material: 30.39 SU/g
Absorbance at 635 nm.

Example 2

Preparation of BPEI/EGDGE/Urease/Carbon Composition with 20% Crosslink Density (Batch 13)

The batch preparation of Example 1 was followed using 3.5 mL EGDGE. The crosslink density was calculated to be approximately 20%.

| Standards | 1 | 2 | 3 | avg | stdev |
|---|---|---|---|---|---|
| 10 | 0.327 | 0.321 | 0.322 | 0.323 | 0.0042 |
| 15 | 0.489 | 0.491 | 0.495 | 0.492 | 0.0014 |
| 20 | 0.66 | 0.666 | 0.661 | 0.662 | 0.0042 |

| | 1 | 2 | 3 | avg | stdev |
|---|---|---|---|---|---|
| Batch 13 | 1.548 | 1.584 | 1.563 | 1.565 | 0.0180 | mg % $NH_3$ in Batch 13 Samples: 46.88
Activity of Material: 23.44 SU/g
Absorbance at 635 nm.

Example 3

Preparation of BPEI/EGDGE/Urease/Carbon Composition with 40% Crosslink Density (Batch 11)

The batch preparation of Example 1 was followed using 7 mL EGDGE. The crosslink density was calculated to be approximately 40%.

| Standards | 1 | 2 | 3 | avg | Stdev |
|---|---|---|---|---|---|
| 10 | 0.314 | 0.306 | 0.312 | 0.31 | 0.0057 |
| 15 | 0.491 | 0.492 | 0.494 | 0.492 | 0.0007 |
| 20 | 0.632 | 0.671 | 0.676 | 0.652 | 0.0276 |

| | 1 | 2 | 3 | avg | Stdev |
|---|---|---|---|---|---|
| Batch 11 | 0.469 | 0.462 | 0.468 | 0.466 | 0.0038 | mg % $NH_3$ in Batch 13 Samples: 14.51
Activity of Material: 7.25 SU/g
Absorbance at 635 nm.

Example 4

Protocol for Measuring Urease Activity

Two (2.0) g of BPEI/EGDGE/Urease/Carbon composition was weighed into a 100 mL volumetric flask with a stir bar. Ten (10) mL of sodium acetatle/sodium chloride bubber solution was added to the flask and stirring began.

Fifteen (15) mL of urea-phosphate solution was added to the flask. After exactly 5 minutes, 15 mL of 1.0 M HCl was added to the flask to quench the reaction. The stir bar was removed and the flask filled to volume with deionized water. The stir bar was replaced and the contents were mixed well.

A 0.45 micron syringe filter was attached to a 3 ml syringe whose plunger has been removed. The syringe was filled with solution from the flask. The plunger was replaced in the syringe and the fluid was pushed through the filter and collected in a clean container. A 20 uL aliquot from the filtered solution was used to test for $NH_4^+$ content in the solution.

Example 5

Determination of Urease Leakage in Albumin Solution

Urease-strip solution was prepared by adding bovine albumin to a 300 mL solution of phosphate buffer at pH 7.0. The albumin was added to a final concentration of 150 mg %.

Solution A was prepared by weighing 2.0 g of BPEI/EGDGE/Urease/Carbon composition into a 100 mL volumetric flask. The flask was then filled to volume with urease-strip solution and stirred for 20 min. A 10 mL aliquot was taken and added to a new 100 mL flask.

Solution B was prepared in the new flask containing the 10 mL of solution A by adding 5 mL of urea phosphate and stirring the solution for exactly 5 min. Then, 10 mL of 1 M HCl was added to quench the reaction. The stir bar was removed and the flask filled to volume with $dH_2O$.

The $NH_4^+$ content was measured as described above.
Calculations:

Activity of solution $B$=mg % $NH_4^+$/100 mL

Activity of solution $A$=(Activity $B$)×10 mL/2.0 g of material

Leakage of urease=(Activity of $A$)/100 mL

Results:
Leakage=0.00148 SU/g-mL

Example 6

Determination of Urease Activity in Albumin Solution

Urea-phosphate solution was prepared by dissolving 1.5 g urea in urease strip solution (phosphate buffer+150 mg % albumin).

Weighed 2.0 g BPEI/EGDGE/Urease/Carbon composition into 100 ml volumetric flask. Added 15 ml of urea-phosphate solution and stirred. After exactly 5 min., 15 mL HCl was added to quench the reaction. The stir bar was removed and the flask filled to volume with $dH_2O$. A 20 uL aliquot was used to test for mg % $NH_4^+$.

| Standards | 1 | 2 | 3 | avg | stdev |
|---|---|---|---|---|---|
| 10 | 0.305 | 0.308 | 0.301 | 0.305 | 0.0021 |
| 15 | 0.477 | 0.468 | 0.472 | 0.472 | 0.0064 |
| 20 | 0.637 | 0.627 | 0.633 | 0.632 | 0.0070 |

| | 1 | 2 | 3 | avg | stdev |
|---|---|---|---|---|---|
| Batch 13 | 1.548 | 1.584 | 1.563 | 1.565 | 0.0181 |

Results:
mg % $NH_3$ in Batch 13 Samples: 14.51
Activity of Material: 7.25 SU/g

Example 7

In these series of examples, Example 1 was essentially repeated except for the noted amounts of each component and, further, the urease used was obtained from Sigma-Aldrich and was in purified form, which can be characterized as having an enzymatic activity of from about 2,700 SU/g to 5,400 SU/g. The crosslinker amount and/or the amine-containing polymer and/or water content used in the reactions were varied to determine the effects of a composition having at least one enzyme, at least one polymer, and at least one crosslinker in the formation of a covalently bond macromolecule. As can be seen below in the results, the urease in purified form still maintained excellent enzymatic stability after a number of days after preparation. This is especially critical when a purified enzyme is used, such as purified urease, because purified urease is considered far less stable than crude urease and can be more susceptible to deactivation upon reaction or modification, such as crosslinking. In these experiments, it was shown that the enzymatic activity can be obtained and be stable over a length of time, such as over 5 days, over 10 days, over 15 days, over 30 days, over 45 days, and the like. The results are summarized below.

Experiment A:
Reagents: 10 g BPEI, 25 ml 5N HCl, 0.1 g Urease, 5 drops DI $H_2O$, 1.75 ml EGDGE Results

| Days After Prep. | Activity of Material (SU/g) |
|---|---|
| 1 | 3.4 |
| 9 | 3 |
| 16 | 2.2 |
| 22 | 4.7 |
| 29 | 4.7 |
| 37 | 3.4 |
| 57 | 2.7 |

Experiment B:
Reagents: 10 g BPEI, 25 ml 5N HCl, 0.3 g Urease, 12 ml DI $H_2O$, 1.75 ml EGDGE Results

| Days After Prep. | Activity of Material (SU/g) |
|---|---|
| 1 | 6.3 |
| 7 | 7.2 |
| 14 | 6.9 |
| 22 | 7.4 |
| 42 | 5.6 |

Experiment C:
Reagents: 10 g BPEI, 25 ml 5N HCl, 0.3 g Urease, 7.5 ml DI $H_2O$, 1.75 ml EGDGE Results

| Days After Prep. | Activity of Material (SU/g) |
|---|---|
| 1 | 7.2 |
| 5 | 7.5 |
| 8 | 9.3 |
| 28 | 6.9 |

Experiment D:
Reagents: 10 g BPEI, 25 ml 5N HCl, 0.3 g Urease, 4.0 ml DI $H_2O$, 1.75 ml EGDGE Results

| Days After Prep. | Activity of Material (SU/g) |
|---|---|
| 1 | 4.5 |
| 2 | 5.1 |
| 22 | 2.9 |

Experiment E:
Reagents: 8 g BPEI, 20 ml 5N HCN, 0.3 g Urease, 6.0 ml DI $H_2O$, 1.40 ml EGDGE Results

| Days After Prep. | Activity of Material (SU/g) |
|---|---|
| 1 | 13.6 |
| 2 | 14 |
| 7 | 12.4 |
| 30 | 25.3 |
| 47 | 13.3 |

Experiment F:

Reagents: 8 g BPEI, 20 ml 5N HCN, 0.3 g Urease, 3.0 ml DI H$_2$O, 1.40 ml EGDGE

Results

| Days After Prep. | Activity of Material (SU/g) |
|---|---|
| 2 | 13.4 |
| 25 | 19.5 |
| 42 | 12.9 |

Experiment G:

Reagents: 6 g BPEI, 15 ml 5N HCl, 0.3 g Urease, 4.0 ml DI H$_2$O, 1.05 ml EGDGE

Results

| Days After Prep. | Activity of Material (SU/g) |
|---|---|
| 5 | 19.7 |
| 11 | 16.3 |

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A dry, solid composition comprising a covalently immobilized enzyme and having enzymatic activity, the composition comprising a reaction product of (i) at least one enzyme, (ii) at least one polymer, and (iii) at least one crosslinker, in a formation of covalently bound macromolecules and wherein the enzyme is urease,
and wherein the enzyme retains greater than 90% enzymatic activity when stored in a dry state, at ambient temperature and pressure, for at least 90 days, compared to enzymatic activity on day of preparation, wherein the composition has a crosslink density of less than 40%.

2. The composition of claim 1, wherein the polymer comprises poly(ethylenimine), poly(propylenimine), poly(allylamine), poly(vinylpyridine), poly(vinylimidazole), poly(l-lysine), or any combination thereof.

3. The composition of claim 1, wherein the polymer is branched poly(ethylenimine).

4. The composition of claim 1, wherein the crosslinker comprises heterobifunctional polyethylene glycol, homobifunctional polyethylene glycol, or any combination thereof.

5. The composition of claim 1, wherein the crosslinker comprises poly(ethylene glycol)diacrylate, tetra(ethylene glycol)diacrylate, poly(ethylene glycol)diglycidyl ether, ethylene glycol diglycidyl ether, dibromohexane, gluteraldehyde, epichlorohydrin, or any combination thereof.

6. The composition of claim 1, wherein the crosslinker comprises one or more functional epoxy groups, one or more functional acrylate groups, one or more functional halide groups, one or more functional carboxyl groups, one or more functional aldehyde groups, or any combination thereof.

7. The composition of claim 1, wherein the crosslinker is ethylene glycol diglycidyl ether.

8. The composition of claim 1, wherein the enzyme is covalently bound to the crosslinker and to the polymer.

9. The composition of claim 1, wherein the enzyme retains at least about 90% of the enzymatic activity compared to non-immobilized enzyme.

10. The composition of claim 1, wherein the composition is a hydrogel.

11. The composition of claim 1, further comprising activated carbon.

12. The composition of claim 11, wherein the activated carbon is present in an amount of from about 1% to about 30% by weight of the composition, the enzyme is present in an amount of from about 30% to about 55% by weight of the composition, the polymer is present in an amount of from about 25% to about 35% by weight of the composition, and the crosslinker is present in an amount to provide a crosslink density of no more than about 40%.

13. The composition of claim 1, further comprising zirconium phosphate.

14. A method for removing a compound from a system containing the compound, the method comprising treating the system with the immobilized enzyme of claim 1, and recovering a system substantially free of the compound.

15. The method of claim 14, wherein the system is a dialysis system.

16. The method of claim 14, further comprising treating the system with one or more ion-exchange material.

17. A sorbent cartridge comprising the composition of claim 1 as a layer in the sorbent cartridge.

18. The sorbent cartridge of claim 17, wherein said sorbent cartridge excludes the presence of alumina adjacent to said composition.

19. A dry, solid composition comprising a covalently immobilized enzyme and having enzymatic activity, the composition comprising a reaction product of (i) at least one enzyme, (ii) at least one polymer, and (iii) at least one crosslinker, in a formation of covalently bound macromolecules, wherein the polymer comprises a polyamine, the crosslinker comprises heterobifunctional polyethylene glycol, homobifunctional polyethylene glycol, or a combination thereof, the enzyme is urease, and wherein said composition has a crosslink density of less than 40%, wherein the enzyme retains greater than 90% enzymatic activity when stored in a dry state, at ambient temperature and pressure, for at least 30 days, compared to enzymatic activity on day of preparation.

20. The composition of claim 19, wherein said urease is raw urease, crude urease or both.

21. The composition of claim 19, wherein said urease is a purified urease.

22. The composition of claim 1, wherein said polymer comprises a polyamine.

23. The composition of claim 1, wherein the polymer and enzyme are crosslinked in a single phase.

24. The composition of claim 1, wherein the polymer and enzyme are crosslinked in an aqueous phase.

25. The composition of claim 1, wherein the dry solid composition comprises dry particles comprising the reaction product.

26. A method for preparing the dry, solid composition of claim 1, the method comprising:
    forming an aqueous mixture of at least one polymer and at least one enzyme, wherein said enzyme is urease;
    adding at least one crosslinker to the aqueous mixture to form a reaction mixture; and
    maintaining the reaction mixture to immobilize the enzyme in a formation of covalently bound macromolecules.

27. The method of claim 26, wherein the polymer comprises a polyamine.

28. The method of claim 26, wherein the polymer comprises poly(ethylenimine), poly(propylenimine), poly(allylamine), poly(vinylpyridine), poly(vinylimidazole), poly(l-lysine), or any combination thereof.

29. The method of claim 26, wherein the polymer is branched poly(ethylenimine).

30. The method of claim 26, wherein the crosslinker comprises heterobifunctional polyethylene glycol, homobifunctional polyethylene glycol, or any combination thereof.

31. The method of claim 26, wherein the crosslinker comprises poly(ethylene glycol)diacrylate, tetra(ethylene glycol) diacrylate, poly(ethylene glycol)diglycidyl ether, ethylene glycol diglycidyl ether, dibromohexane, gluteraldehyde, epichlorohydrin, or any combination thereof.

32. The method of claim 26, wherein the crosslinker comprises one or more functional epoxy group, one or more functional acrylate group, one or more functional halide group, one or more functional carboxyl group, one or more functional aldehyde group, or any combination thereof.

33. The method of claim 26, wherein the crosslinker is ethylene glycol diglycidyl ether.

34. The method of claim 26, wherein the enzyme is crude urease, raw urease or both.

35. The method of claim 26, wherein the polymer is first dissolved in an aqueous solution, then the enzyme is added to the aqueous solution, and then the crosslinker is added to form the reaction mixture.

36. The method of claim 32, wherein a first functional group of the crosslinker reacts with the polymer, and a second functional group of the crosslinker reacts with the enzyme.

37. The method of claim 32, wherein a first functional epoxy group of the crosslinker reacts with an amine group of the polymer and a second functional epoxy group of the crosslinker reacts with an amine group of the enzyme.

38. The method of claim 37, wherein the amine group of the enzyme is from a lysine in the enzyme.

39. The method of claim 26, further comprising blending activated carbon into the mixture.

40. The method of claim 39, wherein the activated carbon comprises from about 1 percent to about 30 percent by weight of the formation.

41. The method of claim 26, further comprising blending zirconium phosphate into the mixture.

42. The method of claim 26, wherein the crosslinker is added in an amount to obtain a crosslink density of from about 5% to about 15%.

* * * * *